(12) United States Patent
McGrattan et al.

(10) Patent No.: US 11,744,779 B1
(45) Date of Patent: Sep. 5, 2023

(54) INFANT FEEDING MEASUREMENT DEVICE

(71) Applicant: nuBorn Medical, Inc., Eden Prairie, MN (US)

(72) Inventors: Katlyn McGrattan, Eden Prairie, MN (US); Kyle Dahlstrom, Eden Prairie, MN (US); John Lindsay, La Grange, IL (US)

(73) Assignee: NUBORN MEDICAL, INC., Eden Prairie, MN (US)

( * ) Notice: Subject to any disclaimer, the term of this patent is extended or adjusted under 35 U.S.C. 154(b) by 256 days.

(21) Appl. No.: 16/823,514

(22) Filed: Mar. 19, 2020

Related U.S. Application Data

(60) Provisional application No. 62/821,173, filed on Mar. 20, 2019.

(51) Int. Cl.
| | |
|---|---|
| *A61J 11/00* | (2006.01) |
| *A61B 5/00* | (2006.01) |
| *A61B 5/03* | (2006.01) |
| *A61J 9/00* | (2006.01) |

(52) U.S. Cl.
CPC ........... *A61J 11/0075* (2013.01); *A61B 5/038* (2013.01); *A61B 5/4205* (2013.01); *A61B 5/4211* (2013.01); *A61B 5/486* (2013.01); *A61B 5/4866* (2013.01); *A61B 5/7246* (2013.01); *A61B 5/7267* (2013.01); *A61B 5/7275* (2013.01); *A61B 5/7282* (2013.01); *A61B 5/742* (2013.01); *A61J 9/00* (2013.01); *A61B 2503/045* (2013.01); *A61B 2562/0247* (2013.01); *A61J 2200/70* (2013.01)

(58) Field of Classification Search
CPC ...... A61J 11/0075; A61J 11/04; A61J 11/045; A61J 9/00; A61J 2200/70; A61B 5/038; A61B 5/4205; A61B 5/486; A61B 5/4866; A61B 5/7246; A61B 5/7267; A61B 5/7275; A61B 5/7282; A61B 5/742; A61B 5/7425; A61B 2503/045; A61B 2562/0247; A61B 5/4211
See application file for complete search history.

(56) References Cited

U.S. PATENT DOCUMENTS

| | | |
|---|---|---|
| 3,790,016 A | 2/1974 | Kron |
| 4,232,687 A | 11/1980 | Anderson et al. |
| 6,033,367 A | 3/2000 | Goldfield |
| 6,109,100 A | 8/2000 | Buckley et al. |
| 8,226,579 B2 | 7/2012 | Barlow et al. |
| 8,413,502 B2 | 4/2013 | Zemel et al. |
| 8,473,219 B2 | 6/2013 | Kaplan et al. |

(Continued)

OTHER PUBLICATIONS

"A Novel System to Study the Coordination of Sucking and Breathing in Newborns During Bottle Feeding", Journal of Latex Class Files, vol. 14, No. 8, (Aug. 2015), 8 pgs.
"NFANT Labs 510(k) Summary", Department of Health & Human Services, (Sep. 9, 2015), 6 pgs.
"Sucking Patterns and Behavioral State in One- and Two-Day Old Full Term Infants", J Obstet Gynecol Neonatal Nurs. 39(5), (Sep. 2010), 519-524.

(Continued)

*Primary Examiner* — Matthew Kremer
(74) *Attorney, Agent, or Firm* — SCHWEGMAN LUNDBERG & WOESSNER, P.A.

(57) ABSTRACT

A system for monitoring infant feeding habit includes a nipple having an embedded pressure sensing passage and pressure sensing opening. The pressure sensing opening is proximate the nipple feeding opening. The pressure sensing passage allows monitoring of change in pressure of infant sucks and swallows throughout feeding.

27 Claims, 14 Drawing Sheets

(56) References Cited

U.S. PATENT DOCUMENTS

| | | | |
|---|---|---|---|
| 8,734,367 | B2 | 5/2014 | Barlow et al. |
| 9,561,002 | B2 | 2/2017 | Lau |
| 9,687,192 | B2 | 6/2017 | Cunningham et al. |
| 9,974,476 | B2 | 5/2018 | Aron et al. |
| 10,085,686 | B2 | 10/2018 | Cunningham et al. |
| 10,299,718 | B2 | 5/2019 | Lau |
| 10,463,577 | B2 | 11/2019 | Lau |
| 2008/0039778 | A1* | 2/2008 | Goldie ............... A61B 5/038 604/67 |
| 2011/0087078 | A1* | 4/2011 | Zemel ............... A61J 9/00 600/300 |
| 2012/0302924 | A1* | 11/2012 | Cunningham ......... A61B 5/228 600/590 |
| 2013/0310661 | A1* | 11/2013 | Jedwab ............... A61B 5/4205 600/301 |
| 2014/0207024 | A1 | 7/2014 | Aron et al. |
| 2015/0196247 | A1* | 7/2015 | Lau ............... G01F 1/363 600/301 |
| 2017/0188936 | A1 | 7/2017 | Lau |
| 2018/0211558 | A1 | 7/2018 | Lau |
| 2018/0243173 | A1* | 8/2018 | Kessels ............... A61J 9/00 |
| 2018/0263549 | A1* | 9/2018 | Rajala ............... A61B 5/4205 |
| 2019/0000371 | A1 | 1/2019 | Cunningham et al. |
| 2019/0216385 | A1 | 7/2019 | Lau |
| 2019/0374438 | A1* | 12/2019 | Dellimore ............... A61J 13/00 |

OTHER PUBLICATIONS

"Technological Solutions and Main Indices for the Assessment of Newborns' Nutritive Sucking: A Review", Sensors 2014, 14, (2014), 634-658.

Capilouto, Gilson J, et al., "Quantifying Neonatal Sucking Performance: Promise of New Methods", Semin Speech Lang 38(2), (Apr. 2017), 147-158.

Lang, William Christopher, et al., "Quantification of Intraoral Pressures During Nutritive Sucking: Methods with Normal Infants", Dysphagia (2011) 26, (2010), 10pgs.

Lau, Chantal, "Development of infant oral feeding skills: what do we know?", Am J Clin Nutr 2016;103(Suppl), (2016), 616S-21S.

McGrattan, Katlyn E, et al., "The physiologic coupling of sucking and swallowing coordination provides a unique process for neonatal survival", Foundation Acta Paediatrica. Published by John Wiley & Sons Ltd 105, (2016), 790-797.

Medoff-Cooper, Barbara, et al., "Sucking Behavior of Preterm Neonates As a Predictor of Developmental Outcomes", J Dev Behav Pediatr vol. 30, No. 1, (Feb. 2009), 16-22.

Wang, Yu-Lin, et al., "Design of wireless multi-parameter monitoring system for oral feeding of premature infants", Med Biol Eng Comput (2016) 54, (2016), 1061-1069.

Wang, Yu-Lin, "Development of a Wireless Oral-Feeding Monitoring System for Preterm Infants", IEEE Journal of Biomedical and Health Informatics, vol. 19, No. 3, (May 2015), 866-873.

* cited by examiner

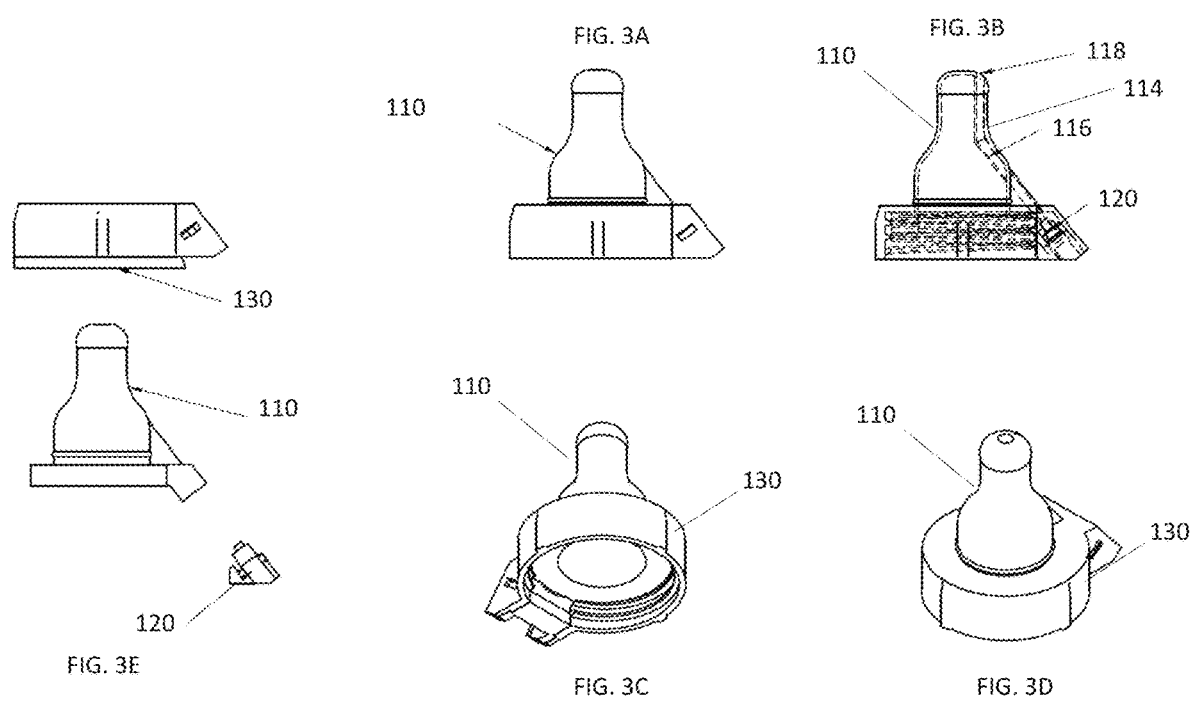

Bottom View

Side View

INFANT FEEDING MEASUREMENT DEVICE

CLAIM OF PRIORITY

This application claims the benefit of priority of McGrattan et al. U.S. Provisional Patent Ser. No. 62/821,173, INFANT FEEDING MEASUREMENT DEVICE, filed Mar. 20, 2019, which is incorporated herein by reference.

BACKGROUND

Infants can benefit from monitoring, such as to help ensure certain developmental markers are met before discharge from the neonatal intensive care unit (NICU) or other hospital stays, including respiratory stability, maintained body temperature, and safe oral feeding. Generally, practitioners treating infants with feeding impairments observe and diagnose feeding performance using subjective clinical observations while feeding the infant from a standard bottle-feeding system. Due to the subjectivity in this assessment approach, it is difficult to complete a valid and reliable assessment to identify impairments and identify optimal interventions to improve the infant's feeding ability.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A-3H illustrate cross sectional and perspective views of a nipple with integrated pressure sensor.

DETAILED DESCRIPTION

The present device can include a bottle nipple, such as can be configured for measuring pressure changes associated with infant sucking and swallowing. This can help allow for monitoring and diagnosis of infant feeding impairments.

Dysphagia, characterized by deficits in sucking and swallowing, is a commonly encountered morbidity among infants with complex medical conditions. For example, 90% of preterm infants suffer from dysphagia at some point in their hospital stay. Left untreated, these deficits cause short and long-term health and financial implications such as cardiopulmonary compromise, nutritional instability, and lengthened hospital stays.

The gold standard in oropharyngeal sucking and swallowing assessment is the videofluoroscopic swallow study. Though it is a valid and reliable method of assessment, it must be used sparingly due to the harmful ionizing radiation it emits. This not only limits the ability to provide early and ongoing oropharyngeal swallowing assessment, but more importantly, limits the ability to provide optimal dysphagia treatment regimens. An objective, non-invasive method of evaluating an infant's feeding abilities can provide clinically significant information to aid in infant feeding management.

A bottle system with an integrated pressure sensor can provide reliable infant feeding data, such as during an infant's pre-feeding and feeding course. A nipple with an embedded pressure sensing channel in fluid communication with a pressure sensor can help allow for effective monitoring of intraoral pressure changes during non-nutritive sucking (NNS) and nutritive sucking (NS) that indicate infant sucking and swallowing characteristics.

Figure 1A:
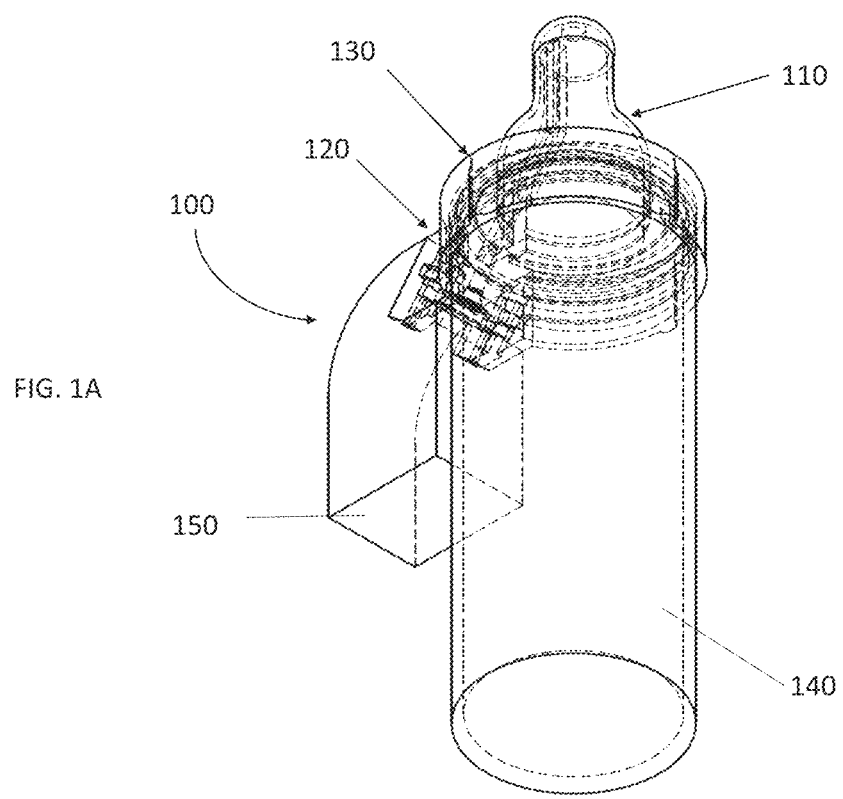
FIGS. 1A-1C illustrate schematic and perspective views of an infant feeding performance system.
Figure 1B:
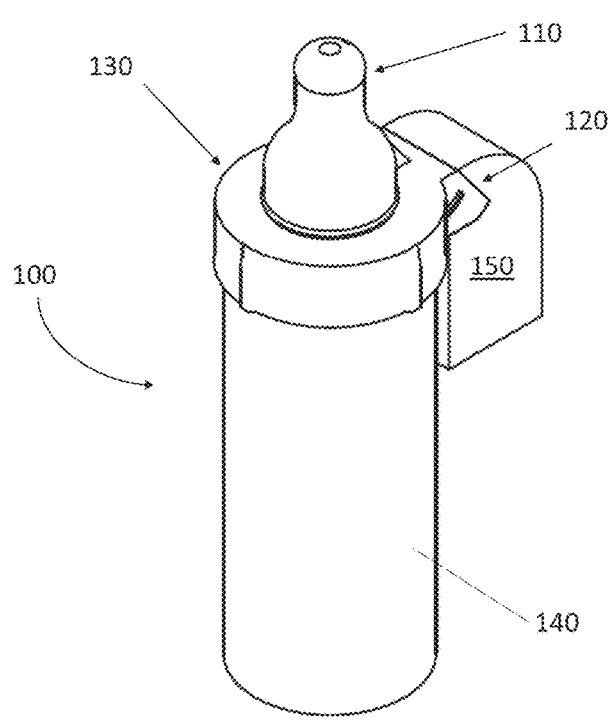
Figure 1C:
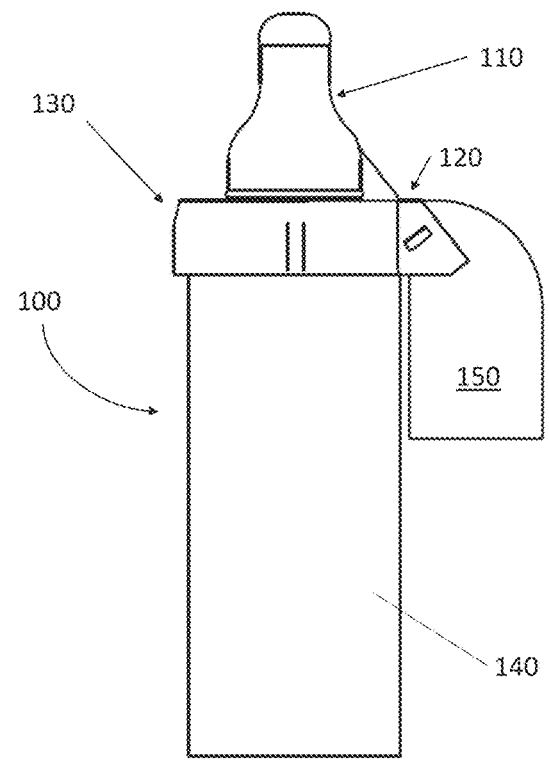
Figure 2A:
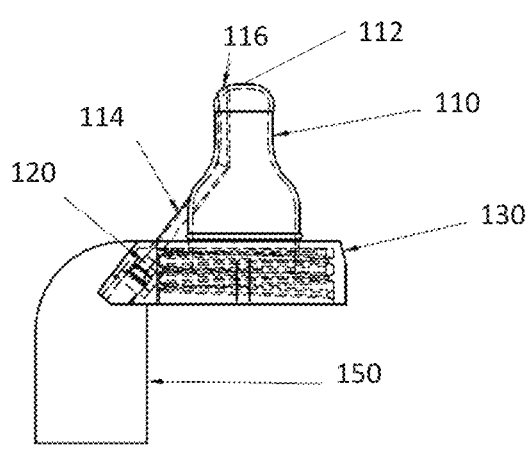
FIGS. 2A-2E illustrate cross sectional and perspective views of a nipple with integrated pressure sensor and electronic module used in the infant feeding performance system of FIG. 1.
Figure 2B:
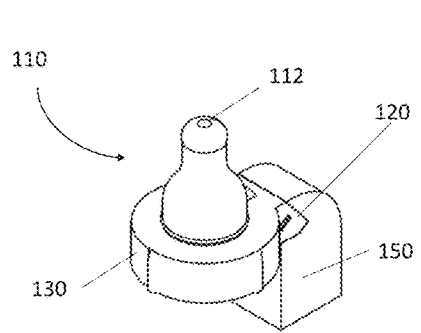
Figure 2C:
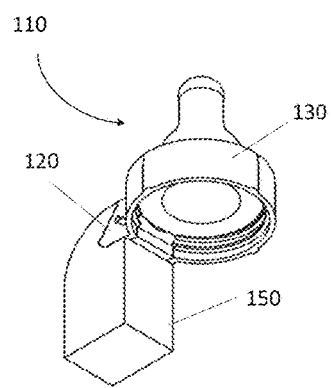
Figure 2D:
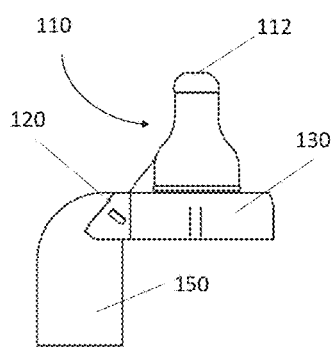
Figure 2E:
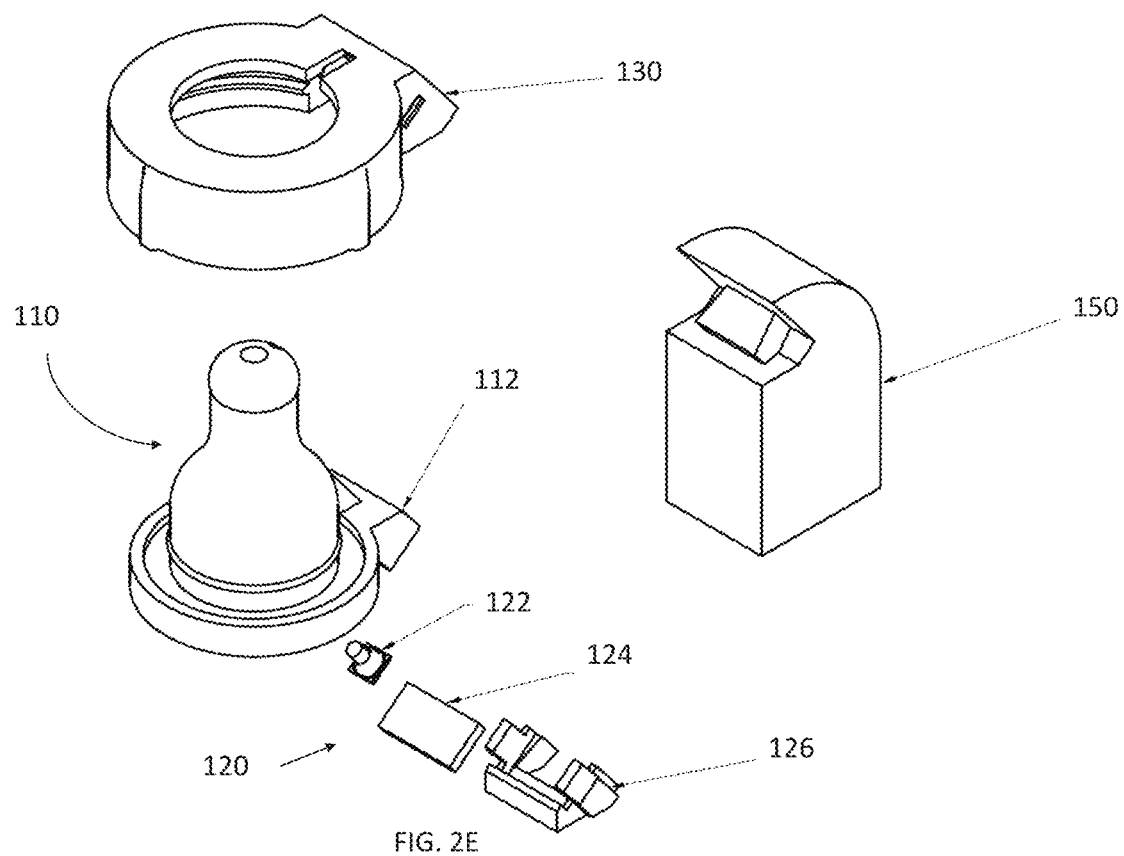
Figure 3F:
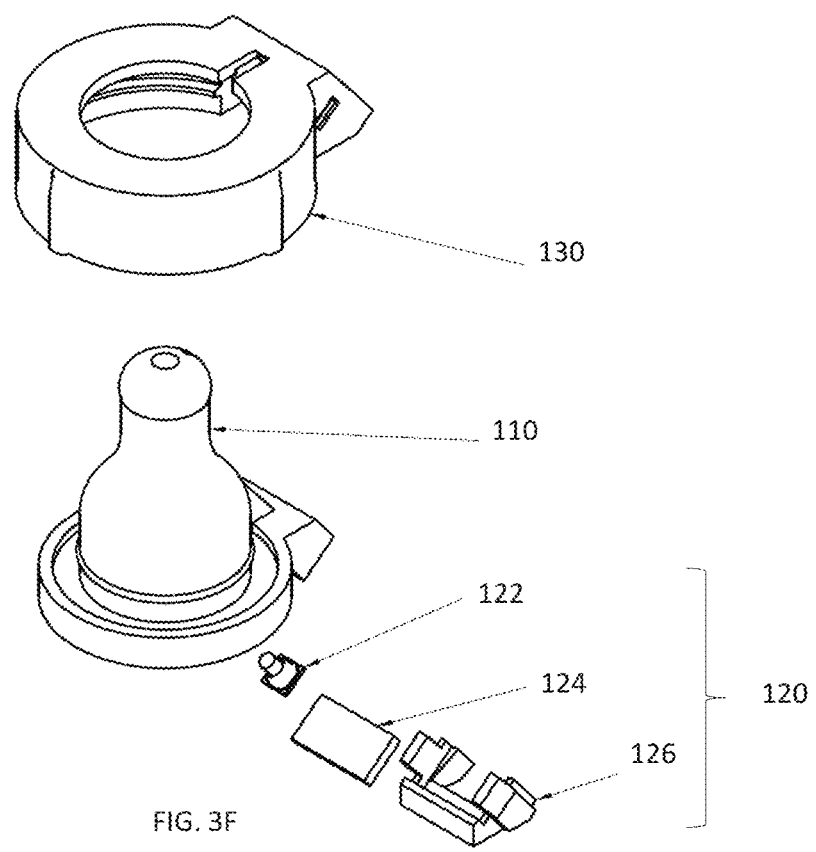
Figure 3G:
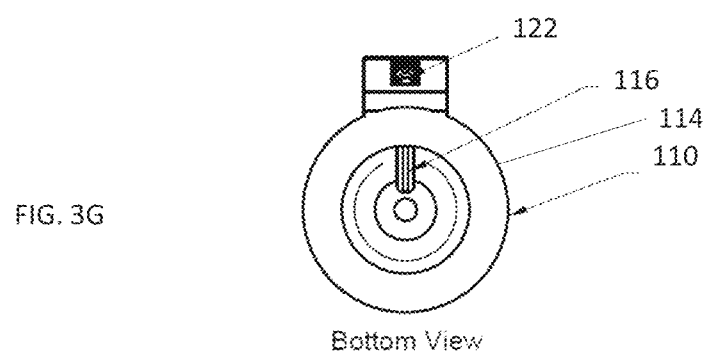
Figure 3H:
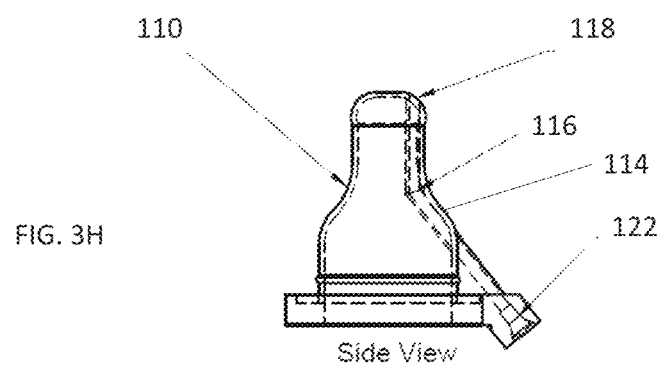

FIGS. 1A-1C show a schematic view of an example of portions of an infant feeding performance measurement system 100. The system 100 can include a nipple 110, a pressure sensor module 120, a collar 130, a bottle 140, and an electronics module 150. The nipple 110 can be secured to the bottle 140, such as by a collar 130. The pressure sensor module 120 can be integrated into the nipple 110 and can be secured by the collar 130. The electronics module 150 can be attached to and can interact with the pressure sensor module 120.

The nipple 110 is configured as a feeding nipple for an infant. The nipple 110 can be made of flexible silicone or other suitable material. The nipple 110 can be sized and shaped to be of standard size and dimension for attachment to a standard infant feeding bottle 140. The nipple 110 can optionally include a feeding hole for infant feeding. The nipple 110 can either be a single use, disposable nipple, or a washable and reusable nipple However, the nipple 110 differs from commercially available disposable nipples in that, among other things, the nipple 110 is configured to sense the intraoral suction pressure as the infant sucks, such as through an embedded pressure sensing channel that can be integrally formed within or along a wall of the nipple and in fluid communication with the pressure sensor module 120. The embedded pressure sensing channel terminates in a secondary opening at the tip of nipple 110, separate from but near enough to the feeding hole (if present) so that the pressure sensing channel can be inserted into the infant's mouth along with the feeding hole during infant feeding to monitor suction pressure produced by the infant, such as during feeding. Illustrative examples of the nipple 110 and the embedded pressure sensing channel are described in more detail with reference to FIGS. 2A-2E and 3A-3H.

The pressure sensor module 120 can be embedded in the nipple 110, such as for measuring, via the pressure sensing channel, the suction produced by the infant during pre-feeding nutritive suck (NNS) and feeding non-nutritive suck (NS) periods. The pressure sensor module 120 can include a pressure sensor configured to monitor, via the pressure sensing channel, infant intraoral suction pressure. The pressure sensor module can transduce this into pressure signal data and communicate that data to the electronics module 150. An illustrative example of the pressure sensor module 120 is described in more detail with reference to FIGS. 4A-4B.

The collar 130 can help secure both the nipple 110 and the pressure sensor module 120 to bottle 140. The collar 130 can include threads or threading, such as can be configured for engagement with compatible threads or threading on the bottle 140, such as to help secure the nipple 110 to the bottle 140. The collar 130 can also include one or more clips, such as to help secure the pressure sensor module 120, the electronic module 150, or both to the nipple 110. An illustrative example of the collar 130 is described in more detail with reference to FIGS. 5A-5B.

The bottle 140 can include a commercially available baby bottle, with which the present nipple 110 can be used. When an infant nutritively sucks (NS), the nipple 110 allows for fluid carried by the bottle 140 to flow from the bottle 140 through the feeding hole in the nipple 110 while concurrently measuring suction pressures using the pressure sensor module 120, such as through the secondary opening in nipple 110 and the integrated pressure sensing channel.

The electronics module 150 can be configured with a snap-fit feature, such as to allow the electronics module 150 to snap into place to mate with the bottle 140 or the collar 130, such as to make selective contact with the pressure sensor module 120 embedded in the nipple 110. The electronics module 150 can include a power source, such as to allow the electronics module 150 to be powered a battery, for example, a coin cell battery.

A user can activate a switch or otherwise initiate use of electronics module 150 for wireless data communication and collection. The electronics module 150 can receive an infant intraoral suction pressure signal, including pressure change data, from the pressure sensor module 120. The electronics module 150 can transmit that data wirelessly to wireless receiver circuitry and, in turn, to signal processing circuitry to analyze the data. The electronics module 150 can, for example, include Bluetooth communication circuitry to wirelessly transmit data.

Safe infant oral feeding involves coordination of sucking and swallowing processes. This involves integration, maturation, and coordination of multiple sensorimotor systems. The infant feeding data generated from pressure suction monitoring by pressure sensor 120 can help allow a clinician to analyze objective data on the infant's feeding abilities.

FIGS. 2A-2E and 3A-3H show an illustrative example of cross-sectional, perspective, and cross-sectional views of the nipple 110, such as can include or define a feeding hole 112, a flexible wall 114 with an embedded pressure sensing channel 116 and a channel opening 118. The nipple 110 is presented with the integrated pressure sensor module 120 (e.g., containing the pressure sensor 122, a sensor circuit board 124, and a sensor clip 126), a collar 130 (e.g., including a snap 132 such as a protrusion or other engagement feature, a first notch 134, and a second notch 136, shown in an exemplary embodiment in FIG. 5A), and the electronics module 150, such as can be used in the infant feeding performance system 100 of FIG. 1. FIGS. 2A-2E and 3A-3H will be described together.

The nipple 110 can include the feeding hole 112, such as extending through the nipple wall 114. The nipple 110 can also include the embedded channel 116, and channel outlet 118. Feeding hole 112 is sized, shaped, or otherwise configured to allow passage of fluid, such as formula or milk, from a bottle (not shown) such as to be dispensed to a feeding infant. The nipple 110 and its constituents can be made, for example, by injection molding.

When non-nutritive suck (NNS) is of interest, there is no feeding hole in the nipple 110. In this case, the other components of the nipple 110, including the flexible nipple wall 114, the embedded pressure sensing channel 116, and the channel opening 118 are still present. However, the nipple 110 can optionally be filled in with silicone instead of hollow, as no passage of fluid or milk is needed.

The nipple wall 114 forms the curved shape of the nipple 110. The nipple wall 114 is made of silicone or other appropriate, flexible material for infant feeding. The embedded channel 116 is a pressure sensing passage within nipple 110. The embedded channel 116 lies integrated within or integrated adjacent to the nipple wall 114. The embedded channel 116 is integrally formed with nipple wall 114 from the pressure sensor 120 to the channel outlet 118. The embedded channel 116 is isolated from and does not open into the interior of the nipple 110. In this way, the embedded channel 116 does not draw fluid from the bottle when an infant is feeding on nipple 110, although some fluid may enter the embedded channel via the channel outlet 118, such as ancillary to the infant's feeding via the feeding hole or from within the infant's mouth. The size of embedded channel 116 is based on the size of the pressure sensor 122 in the pressure sensing module 120. For example, the embedded channel can have a diameter slightly smaller than the pressure sensors 122 to allow for sealing around pressure sensing module 120. The diameter of the embedded pressure sensor can be in a range from about 1 mm to about 4 mm. The embedded channel 116 can be made, for example, through injection molding when the entirety of the nipple 110 is made through a mold process.

The channel outlet 118 is located nearby the feeding hole 112 on the feeding end of nipple 110. The channel outlet 118 allows for monitoring of the pressure of infant sucking. Additionally, this data can be used to monitor infant swallowing. When the infant sucks on the nipple 110, the infant's mouth covers both the feeding hole 112 and the channel outlet 118. Thus, changes in pressure produced by infant sucking during feeding can be contemporaneously detected, monitored, or captured by the pressure sensor, such as via pressure changes in the embedded channel 116 without interrupting the infant's feeding via the feeding hole 112.

Figures 4A, 4B:
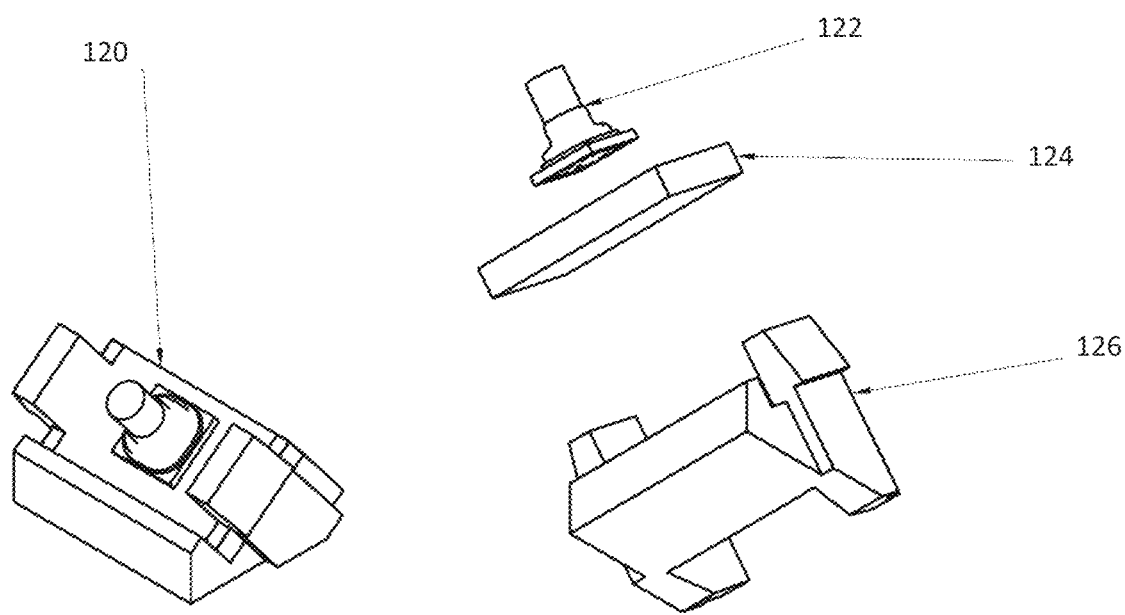
FIGS. 4A-4B illustrate schematic and exploded views of a pressure sensor for use in the system of FIG. 1.

FIGS. 4A-4B show perspective and exploded views of an example of the pressure sensor module 120 such as can be configured for use with the nipple 110. The pressure sensor module 120 can include the pressure sensor 122, a sensor interface circuit board 124, and a sensor clip 126.

The pressure sensor 122 is capable of detecting and transducing pressure changes in the embedded channel 116 when an infant is feeding on the nipple 110. The pressure sensor 122 can be coated in or covered by silicone or a similar membrane, such as to allow fluid-impervious sealing of the pressure sensor 122 within the pressure sensor module 120 and isolation from liquids within the bottle assembly as a whole or introduced into the embedded channel via the infant's mouth.

The pressure sensor 122 can interact with the sensor circuit board 124. When the pressure sensor 122 senses a change in pressure from the embedded channel 114, the pressure signal is transduced into an electrical signal at the sensor circuit board 124 and transmitted to the electronics module 150, which in turn wirelessly transmits the pressure data to receiver circuitry for analysis by a signal processing circuit, such as described with reference to FIGS. 6-7. The sensor clip 126 can secure the sensor circuit board 124 and the pressure sensor 122 into the pressure sensor module 120.

Figure 5A:
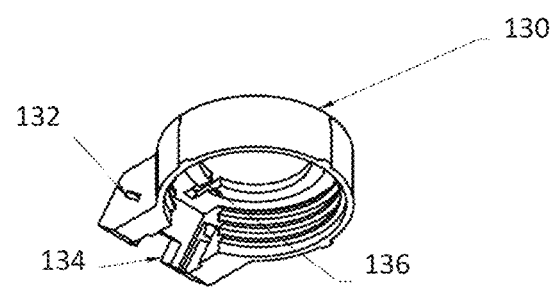
FIGS. 5A-5B illustrate bottom and top views of a collar for attaching a nipple with integrated pressure sensor to a bottle.
Figure 5B:
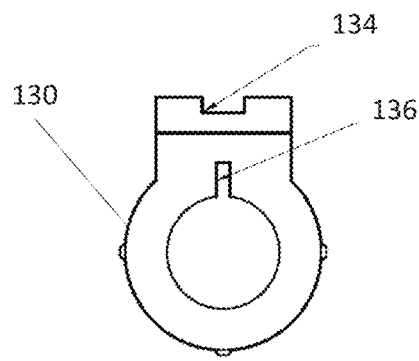

FIGS. 5A-5B show bottom and top views of an example of the collar 130 such as for attaching a nipple 110, including the integrated pressure sensor module 120, to a bottle. The collar 130 can include a snap 132, a first notch 134, and a second notch 136. The collar 130 is threaded to be fitted to a commercially available bottle such as the bottle 140. Unlike commercially available bottle collars, the collar 130 fits over the pressure sensor module 120. Additionally, the collar 130 can help aid in aligning the bottle 140 and the nipple 110. Unlike a traditional bottle nipple, the assembly 100 can be properly aligned for the pressure sensor 122 to get an accurate read of suction pressure from infant feeding.

The snap 132 can provide a snap-in securement mechanism, such as for attaching the pressure sensor 122 within the pressure module 120 on the collar 130. The first notch 134 can provide an indent that can help serve to align the pressure sensor module 120 with the nipple 110 and the bottle 140. The second notch 136 can help aid in aligning the nipple 110 within the collar 130 when assembled. The collar 130 can hold the nipple 110, the pressure sensor module 120, and the bottle 140 together.

Figure 6:
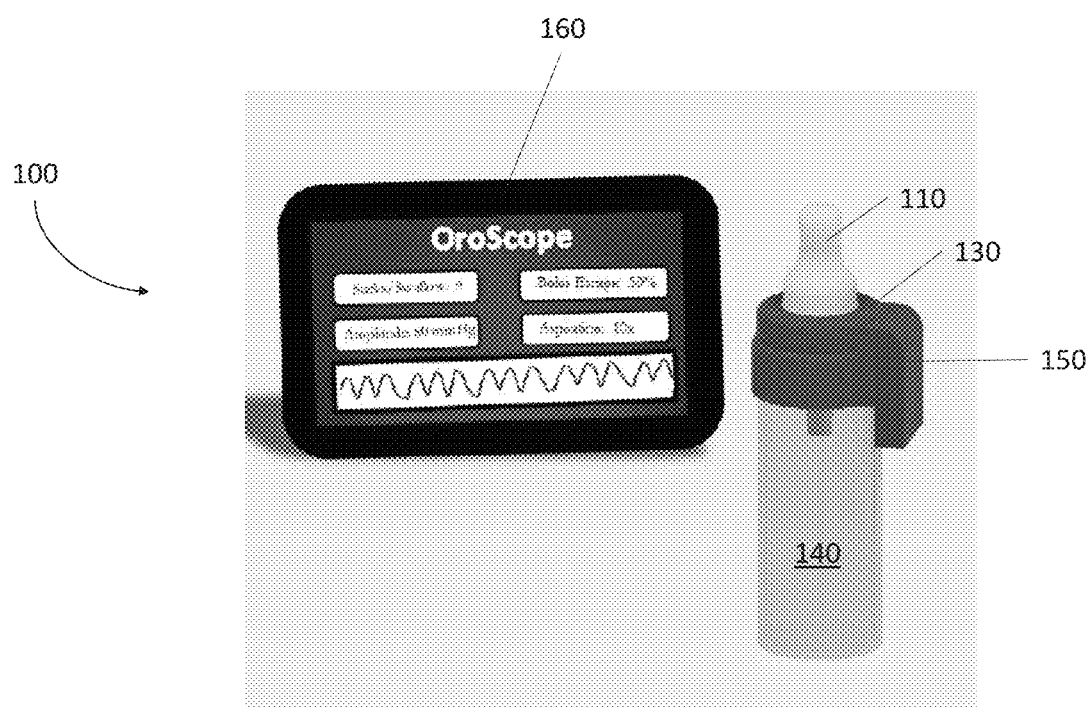
FIG. 6 illustrates a perspective of a software application and bottle for monitoring infant feeding habits based on data from an infant feeding system.

FIG. 6 shows an example of aspects of a signal-processing software application 160 hosted on computing device 180 and the bottle 140 for monitoring one or more infant feeding characteristics based on infant suction pressure data from the infant feeding system 100 of FIG. 1.

The software application 160 acts as a user interface and data display in communication with the pressure sensor module 120, such as via the electronics module 150. Suction pressure measurements generated during infant feeding are transmitted to a mobile or other computing device 180 hosting the software application 160. The resulting pressure signal, or infant feeding data extracted therefrom, or both, can be displayed, such as to permit clinician viewing, interpretation, or action. Information from past infant feedings can also be securely transferred, stored, and retrieved by authorized users, such as from a cloud-based database, such as for comparison to previous data from the same infant, or for comparison to previous data from a population or a selected subpopulation of infants, or both.

Figure 7:
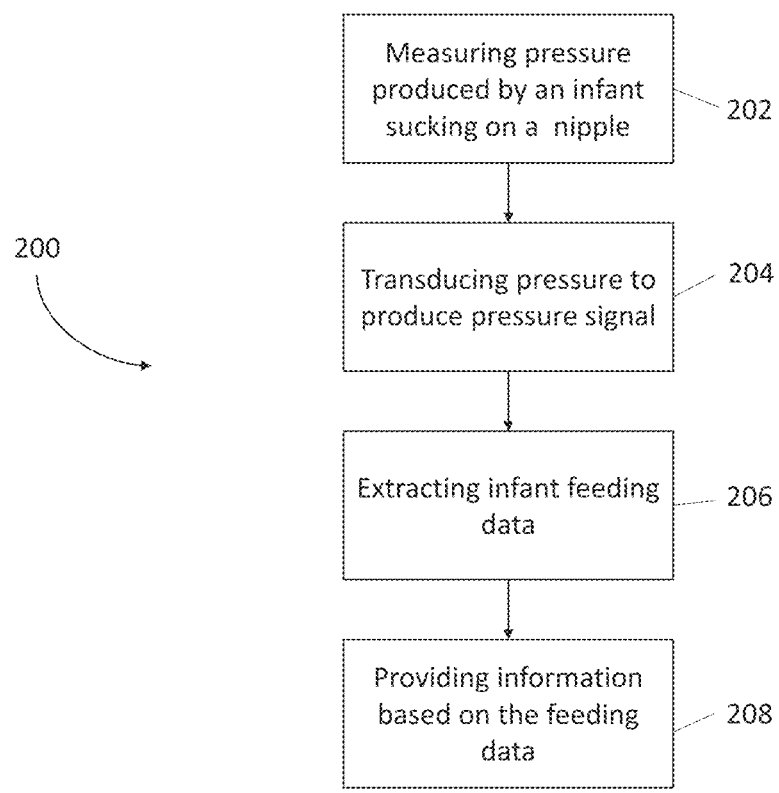
FIG. 7 illustrates a flow chart depicting a method of monitoring infant feeding habits.

FIG. 7 is a flowchart depicting a method 200 of monitoring infant feeding, such as with the system 100 of FIG. 1. Method 200 can include the steps of measuring pressure (step 202), transducing pressure (step 204), extracting infant feeding data (step 206), and providing information based on the pressure signal (step 208).

In step 202, pressure produced by an infant sucking on a nipple is measured. The difference in pressure due to the infant's sucking is measured via a pressure sensing passage (such as the embedded channel 116 of the nipple 110) such as can be located integrally in the nipple wall. The pressure sensing passage can be distinct from the feeding passage that is defined by the nipple wall and outlets at a feeding hole. For example, the pressure sensing passage can provide a separate outlet near to the feeding hole such that the infant's mouth can cover both the feeding hole (if present) and the pressure sensing passage outlet, when sucking. This can help provide an accurate assessment of the pressure produced by the infant's sucking on the nipple.

In step 204, the pressure measured in step 202 is transduced by a pressure sensor (such as the pressure sensor 122), such as can be located at the other end of the pressure sensing passage, away from the pressure sensing passage outlet that is located near the top of the nipple. This transducing by the pressure sensor can produce an electrical pressure signal representative of the pressure variations in the pressure sensing passage that are measured by the pressure sensor.

In step 206, infant intraoral pressure data can be extracted from the pressure signal. For example, both infant sucking and infant swallowing data can be extracted, and pressure signal variations can be correlated to one or more infant feeding parameters.

Depending on the specific infant being studied and what the desired outcome is, information extracted from the pressure signal can include, among other things, one or any combination of suck amplitude, suck generation, suck release rate, suck duration, suck generation duration, milk ejection pressure, suck integral, suck burst length, burst break length, suck peaks metric, suck spectral arc length, suck frequency, lingual fasciculations, sucks per swallow, suck rhythmicity, swallow frequency, swallow rhythmicity, oral bolus hold, presence and initiation of pharyngeal swallow, tongue base retraction, pharyngeal stripping wave, soft palate elevation, nasopharyngeal regurgitation, pharyngeal residue, bolus airway entry penetration, bolus airway entry aspiration, upper esophageal segment opening, or the like. Such information can be automatically extracted from the pressure signal, such as via the signal-processing circuitry, without requiring user-intervention, or semi-automatically, such as can involve some user input or intervention.

Infant feeding data can be additionally or alternatively be generated manually, such as by a human clinician evaluating the infant's feeding by observing the infant during the clinical feeding evaluation, observing the pressure signal, or by observing the internal physiology on the videofluoroscopic swallow study. In clinical feeding evaluations, the human clinician practitioner can bottle-feed the infant and observe one or more subjective signs of feeding impairment. Information such as sucks per swallow, stress cues, respiratory-swallow coordination, suck strength, lingual fasciculations, and signs of bolus airway entry can be visually observed by observing the infant clinically. Additionally, the practitioner can optionally monitor milk ingestion variable such as proficiency, efficiency, overall transfer, rate of transfer, or feed duration, which can be correlated to collected pressure data.

Sucks per swallow is the number of times an infant sucks before swallowing. This can be palpated while holding the bottle in clinical feeding evaluations based on the pull of the infant on the bottle nipple. The number of sucks per swallow can vary during or throughout an infant feed.

Suction strength refers to the amplitude of the infant's sucking. Clinician feeding evaluation by visual observation allows for observance of very strong or very weak sucks, but not refined gradients.

Lingual fasciculations of the tongue are tremor-like movements. These can be manually palpated while holding the bottle during the clinical feeding evaluations.

Bolus airway entry includes penetration or aspiration. Aspiration is bolus entry below the vocal folds. Penetration is bolus entry above the vocal chords. Clinical signs of bolus airway entry include coughing, choking, apnea, bradycardia, or infant stress cues. However, some infants aspirate without any outward visually-observable signs (silent aspiration).

Videofluoroscopic swallow studies are x-ray videos of an infant feeding to show infant sucking and swallowing physiology and its effects on bolus flow. The infant is fed barium, instead of milk, to allow for visualization of bolus flow as it moves through the oral cavity and pharynx. A small sample of swallows are fluoroscopically observed to limit infant radiation exposure. By visually observing videofluoroscopic images, feeding characteristics can be visually deduced by the clinician. These include, but are not limited to, sucks per swallow, oral bolus hold, initiation of swallow, tongue-based retraction, pharyngeal stripping wave, pharyngeal residue, pharyngoesophageal segment opening, and bolus airway entry.

Sucks per swallow refers to the number of times an infant sucks before initiating a swallow. This can be visually observed directly during the clinical assessment, or through the videofluoroscopic swallow study.

Oral bolus hold refers to the infant's ability to maintain the bolus in their oral cavity prior to swallowing. If the liquid spills into the throat before swallowing, it places the infant at higher risk for the liquid to spill into the airway and cause bolus airway entry This can be observed on videofluoroscopic swallow study.

Initiation of swallow can be viewed on videofluoroscopic swallow study. This marks the time when the pharyngeal muscles contract to begin closing off the infant's airway. Optimal initiation occurs when the liquid is high in the infant's mouth so it is less likely to go into their lungs. In contrast, if the infant initiates a swallow when the liquid is far down the throat, such as near the pyriform sinuses, there is a higher chance of the bolus going down towards the lungs (bolus airway entry).

Tongue based retraction can be observed on the videofluoroscopic swallow study. The base of the tongue pushes back posteriorly into the pharynx, allowing pressure to be created to push the bolus down into the esophagus. The extent of tongue-based retraction is judged by the amount of liquid between the base of the tongue and the back wall of the throat (posterior pharyngeal wall) at maximal contraction. If the tongue does not retract far enough, the bolus may remain in the throat after the swallow.

Pharyngeal stripping wave can be observed on the videofluoroscopic swallow study. This occurs when the pharynx (throat) muscles contract in sequence starting at the top of the throat and down towards the stomach. These contractions occur in a wave-like movement. This can be observed via x-ray video.

Pharyngeal residue can be observed on the videofluoroscopic swallow study. Pharyngeal residue occurs when the infant has impairments in tongue-base retraction, pharyngeal stripping wave or pharyngoesophageal segment opening.

Pharyngoesophageal segment opening can be observed on the videofluoroscopic swallow study. The pharyngoesophageal segment sits at the top of the esophagus. If this does not open adequately to allow the bolus to pass into the esophagus, residue can build up in the throat and insufficient nutrition can get to the stomach.

Bolus airway entry (penetration or aspiration) can be observed on the videofluoroscopic swallow study. As described above, if deficits in sucking or swallowing physiology exist, the ingested material can be penetrated or aspirated.

The types of infant feeding characteristics and challenges described herein can be monitored by a practitioner through direct visual clinical feeding evaluation, a videofluoroscopic swallow study, or both. The practitioner observances and images produced from these studies can be correlated to the infant intraoral suction pressure signal data being concurrently monitored using the nipple with the embedded pressure sensing passage.

Based on these correlations, a machine learning model can be trained to extract the infant feeding data from the pressure signal data, such as by using as training data for the machine learning model the correlated information between the measured pressure changes from infant sucks and swallows as correlated with the one or more infant feeding characteristics determined by the clinician directly or via videofluoroscopic images. Thus, the measured pressure signals can be correlated to various feeding impairments.

When the practitioner is initially correlating the observed feeding characteristics or impairments through the videofluoroscopic swallow or clinical feeding evaluation, practitioner observed infant feeding characteristics or impairments can be input into a user interface (such as software application 160) to associate the feeding impairments or habits with pressure data concurrently collected by the nipple system (100). These observed infant feeding characteristics can be input into the user interface with specific time tags to correlate the feeding habits with pressure signals measured during particular time periods.

After the clinician has manually entered metrics into the user interface corresponding to certain measured pressure signals, the machine learning model can be trained using such metrics together with the measured pressure signals. The trained machine learning model can then be used to extract infant feeding characteristics from the pressure signal data, such as without requiring clinician direct visual or videofluoroscopic information. Using the trained machine learning model, instead of videofluoroscopy can help avoid exposing the infant to x-ray radiation. The machine learning model can be trained using human clinician input as "ground truth" training data. The machine learning model can be additionally or alternatively trained by, for instance, a conditional generative adversarial network (CGAN) machine learning technique.

The trained machine learning model can then be used to evaluate infant feeding characteristics without requiring additional practitioner input. For instance, the machine learning model can be used to monitor infant intraoral suction characteristics during or throughout a pre-feeding or feeding period. The machine model can be trained to recognize feeding characteristics such as, suck amplitude, suck generation, suck release rate, suck duration, suck generation duration, milk ejection pressure, suck integral, suck burst length, burst break length, suck peaks metric, suck spectral arc length, suck frequency, lingual fasciculations, sucks per swallow, suck rhythmicity, swallow frequency, swallow rhythmicity, oral bolus hold, presence and initiation of pharyngeal swallow, tongue base retraction, pharyngeal stripping wave, soft palate elevation, nasopharyngeal regurgitation, pharyngeal residue, bolus airway entry penetration, bolus airway entry aspiration, upper esophageal segment opening, or the like The trained machine learning model can use the pressure signal and feeding characteristic data to create metrics for infant feeding. For instance, a single infant or a group of infants can be assigned a risk for hospital readmission metric based on the model's produced information.

These metrics can be used to provide useful information to the infant's guardian, such as a time to hospital discharge, an alternative nutrition need metric at discharge, an alternative nutrition need metric at one or more specified post-discharge time intervals, a future developmental delay metric, a risk of future oral nutrition deficit metric, a risk of future cardiopulmonary stability metric, or a risk of hospital readmission for feeding difficulty metric. Alternatively, or additionally, these metrics can be used to help diagnose dysphagia-associated etiologies and neurologic disorders or syndromes based on their corresponding phenotypes, such as cleft of hard or soft palate, spinal muscular atrophy, cerebral palsy, Down syndrome, DiGeorge syndrome, Pierre Robin sequence, a specified genetic anomaly, congenital heart defect, or a specified neurologic impairment.

Finally, these metrics can be useful in determining prescribed care and practitioner recommendations, such as bottle nipple type, bottle type, feeding position, feeding duration, pacing, volume per feeding session, feeding fluid characteristics, alternative nutrition, or oral motor therapy, that will be useful for infant care during and after hospital stay.

The collected pressure data can be evaluated with regards to an infant relative to a peer group or population group. General metrics that can be created based on the collected data include rate of transfer metrics, overall transfer metrics, or other appropriate metrics.

Finally, in step 208, the infant feeding data is displayed as information for a user, for other signal processing, for storage, or for tracking.

The collected data from step 206 can be further analyzed to provide information indicating time to hospital discharge, alternative nutrition or feeding needs after discharge, specific post-discharge feeding intervals, developmental delay metrics, the risk of hospital readmission, and more. The data can be used to correlate practitioner recommendations such as bottle nipple types, bottle types, feeding positions, feeding duration, volume per feeding session, types of feeding fluid, oral motor exercises, or alternative nutrition plans.

Figure 8:
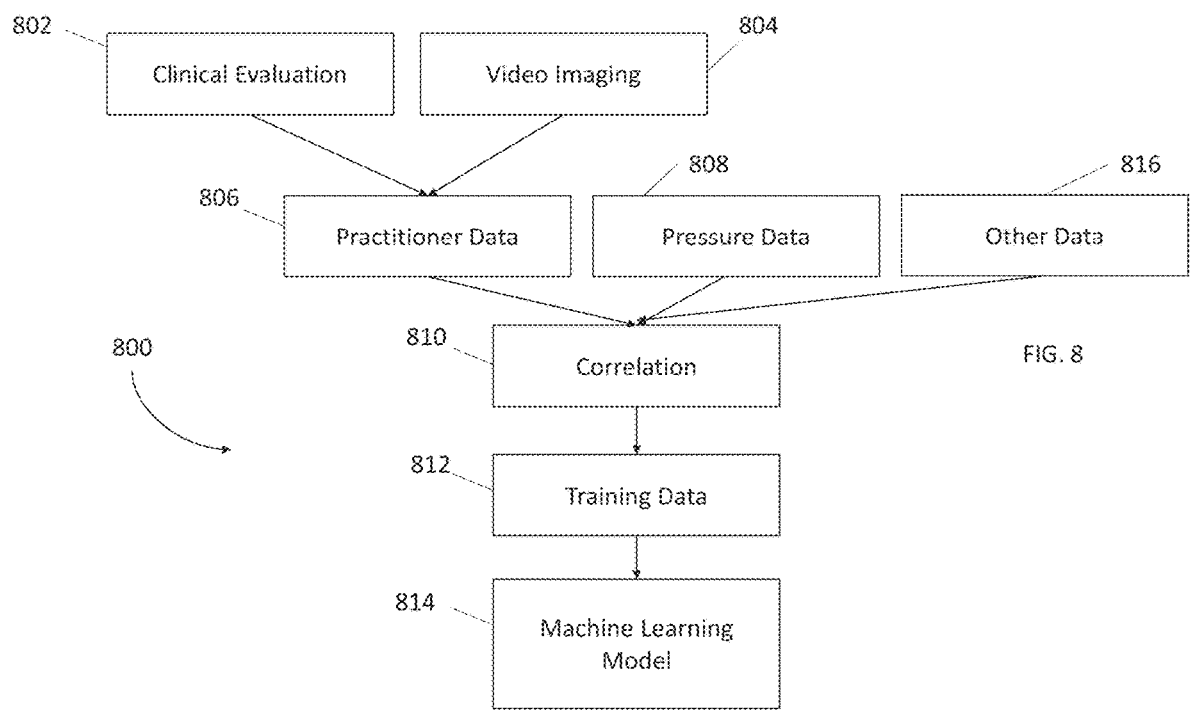
FIG. 8 illustrates a block diagram showing a method of monitoring infant feeding habits with an infant feeding system.

Additionally, the data from step 206 can be used to diagnose an indication of dysphagia-associated diseases such as craniofacial deficits, neurologic disorders, associated syndromes, genetic anomalies, or congenital heart deficits FIG. 8 illustrates the creation of a machine learning model through a block diagram (800). In FIG. 8, the practitioner evaluates the infant either through manual visual inspection (clinical evaluation 802), through videofluoroscopic swallow study x-ray imaging (video imaging 804), or a combination thereof. Simultaneously, pressure data is being collected (808) through the nipple system (such as nipple 110 discussed above). The practitioner correlates this data (0.810). Through this, training data (812) is provided to create a machine learning model (814). Optionally, other data inputs (816), such as heart rate or physiological monitoring of the infant can additionally be correlated to the pressure data and practitioner data.

Figure 9:
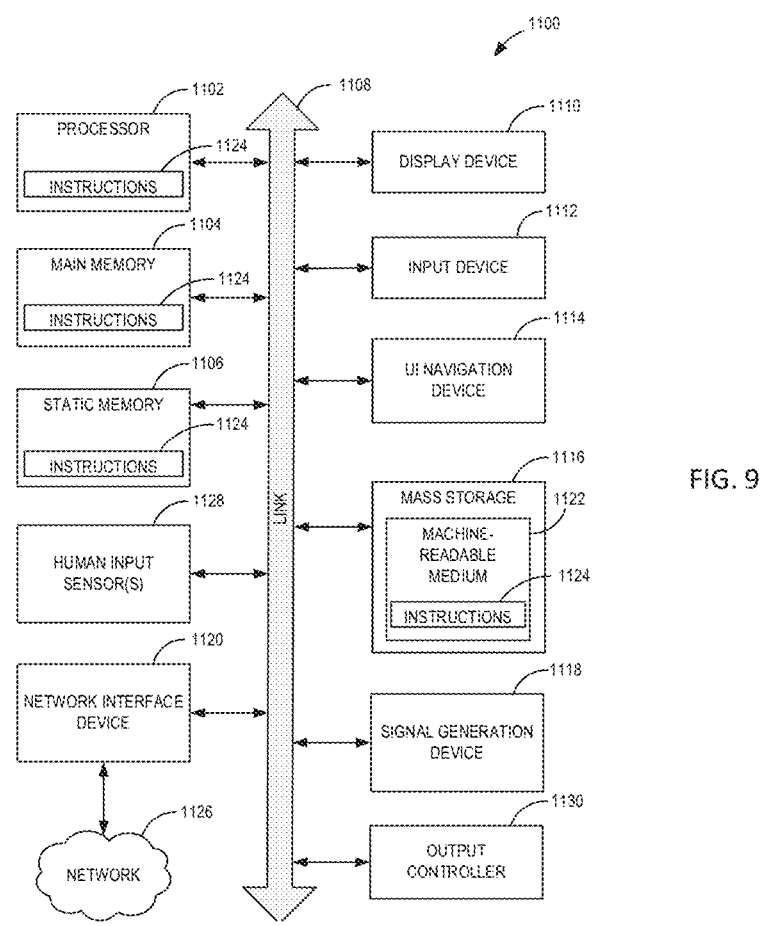
FIG. 9 illustrates a block diagram of an embodiment of a device or machine on which one or more of the methods as discussed herein can be implemented, such as for using a statistical or machine learning technique for sampling a posterior distribution such as for providing uncertainty information associated with a reconstructed image.

FIG. 9 illustrates a block diagram of an embodiment of a device or machine 1000 on which one or more of the methods as discussed herein can be implemented. One or more items of the image processing device 112 can be implemented by the machine 1000. The machine 1000 can operate as a standalone device or may be connected (e.g., networked) to other machines. The image processing device 112 can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 can include processing circuitry 1002 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. A datum or data associated with the described methods can be stored in or retrieved from such memory and initialized or updated as desired to carry out the methods described herein. The machine 1000 (e.g., computer system) may further include a video display unit 1010 (e.g., a liquid crystal display (LCD) or a cathode ray tube (CRT)). The machine 1000 can also include an alphanumeric input device 1012 (e.g., a keyboard), a user interface (UI) navigation device 1014 (e.g., a mouse), a disk drive or mass storage unit 1016, a signal generation device 1018 (e.g., a speaker) and a network interface device 1020.

The disk drive unit 1016 can include a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated can include an output controller 1028. The output controller 1028 manages data flow to/from the machine 1000. The output controller 1028 can sometimes be called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM). Electrically Erasable Programmable Read-Only Memory (EEPROM), and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP).

Examples of communication networks include a local area network ("LAN"), a wide area network ("WAN"), the Internet, mobile telephone networks. Plain Old Telephone (POTS) networks, and wireless data networks (e.g., WIFI and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein. "communicatively coupled between" means that the entities on either of the coupling must communicate through an item therebetween and that those entities cannot communicate with each other without communicating through the item.

An infant feeding and monitoring system based on a nipple with an embedded channel and pressure sensor allows for non-invasive measurement of sucking and swallowing during infant feedings or testing sessions. Moreover, the system allows for real time assessment of feeding impairment and effects of feeding treatments.

Clinical workflow in the NICU need not be interrupted when a practitioner must measure infant feeding habits. In contrast, the nipple and pressure sensor system can be efficiently attached to a standard bottle and used quickly to collect data on infant feeding habits.

Notes and Examples

The following, non-limiting examples, detail certain aspects of the present subject matter to solve the challenges and provide the benefits discussed herein, among others.

Example 1 is an apparatus including an infant feeding nipple comprising a flexible nipple wall extending between a feeding end and a bottle end, the feeding end defining an opening of a feeding passage, the feeding passage extending through the nipple wall to receive fluid for feeding the infant, the nipple further comprising a pressure-sensing passage, integrally formed within or along the nipple wall and extending from the feeding end to an opening at a pressure sensor location.

Example 2 includes the apparatus of Example 1, further including a pressure sensor located in or adjacent the nipple, the pressure sensor in fluid communication with the pressure sensing passage to transduce a pressure in the pressure sensing passage into a transduced pressure signal.

Example 3 includes the apparatuses of any one or any combination of Examples 1-2, further including a communication circuitry module electrically connected to the pressure sensor and configured to process the pressure signal to provide infant feeding data.

Example 4 includes the apparatuses of any one or any combination of Examples 1-3, further including a user interface for receiving information from the communication circuitry module and displaying infant feeding data to a user.

Example 5 includes the apparatuses of any one or any combination of Examples 1-4, wherein the communication circuitry module and the user interface respectively include wireless communication circuitry to communicate therebetween information based on the pressure signal.

Example 6 includes the apparatuses of any one or any combination of Examples 1-5, further including, further comprising a collar for attaching the nipple to a bottle at the bottle end of the nipple, wherein the collar fits around the pressure sensor.

Example 7 includes the apparatuses of any one or any combination of Examples 1-6, wherein the collar includes a snap for securing the pressure sensor, a first notch for aligning the pressure sensor with the collar, and a second notch for aligning the nipple with the collar.

Example 8 includes the apparatuses of any one or any combination of Examples 1-7, further including a bottle configured to be attached to the nipple by the collar.

Example 9 includes the apparatuses of any one or any combination of Examples 1-9, wherein the pressure sensor includes an elastic membrane.

Example 10 includes the apparatuses of any one or any combination of Examples 1-9, wherein the pressure-sensing opening is adjacent the opening of the feeding passage.

Example 11 includes a method for monitoring infant feeding. The method includes measuring pressure, produced by an infant sucking on a nipple, via a pressure sensing passage located integral to the nipple wall and separate from a feeding passage extending through the nipple wall, transducing pressure measured by a pressure sensor in communication with the pressure sensing passage into a transduced pressure signal, extracting infant feeding data from the pressure signal, and providing information based on the pressure signal for one or any combination of display to a user, further signal processing, storage, or tracking.

Example 12 includes the method of Example 11, wherein extracting infant feeding data includes extracting information about one or any combination of infant sucking or swallowing.

Example 13 includes the methods of any one or any combination of Examples 11-12, wherein extracting infant feeding data includes correlating the pressure in the passage to one of a nonnutritive suck or a nutritive suck.

Example 14 includes the methods of any one or any combination of Examples 11 13, wherein extracting infant feeding data comprises evaluating or displaying, or both, one or any combination of suck amplitude, suck generation, suck release rate, suck duration, suck generation duration, feeding duration, milk ejection pressure, suck integral, suck burst length, burst break length, suck peaks metric, suck spectral are length, suck frequency, lingual fasciculations, sucks per swallow, suck rhythmicity, swallow frequency, swallow rhythmicity, oral bolus hold, initiation of pharyngeal swallow, tongue base retraction, pharyngeal contraction, tongue base retraction, pharyngeal stripping wave, soft palate elevation, nasopharyngeal regurgitation, pharyngeal residue, bolus airway entry penetration, bolus airway entry aspiration, or upper esophageal segment opening.

Example 15 includes the methods of any one or any combination of Examples 11-14, wherein providing information based on the pressure signal includes predicting and displaying one or any combination of: a time to hospital discharge, an alternative nutrition need metric at discharge, an alternative nutrition need metric at one or more specified post-discharge time intervals, a future developmental delay metric, a risk of future oral nutrition deficit metric, a risk of future cardiopulmonary stability metric, or a risk of hospital readmission for feeding difficulty metric.

Example 16 includes the methods of any one or any combination of Examples 11-15, further including evaluating or displaying, or both, an infant feeding metric of a particular infant being monitored relative to a peer group or population group, the infant feeding metric including one or any combination of a proficiency metric, an efficiency metric, a rate of transfer metric, or an overall transfer metric.

Example 17 includes the methods of any one or any combination of Examples 11-16, further including identifying or prioritizing one or more recommendations to improve or maximize infant feeding performance, the one or more recommendations including one or any combination of: bottle nipple type, bottle type, feeding position, feeding duration, pacing, volume per feeding session, feeding fluid characteristic, oral motor exercises, or alternative nutrition.

Example 18 includes the methods of any one or any combination of Examples 11-17, further including evaluating or displaying, or both, an indication of an infant feeding phenotype according to a dysphagia-associated disease state including one or any combination of: cleft of hard or soft palate, spinal muscular atrophy, cerebral palsy, Down syndrome. DiGeorge syndrome. Pierre Robin sequence, a specified genetic anomaly, congenital heart defect, or a specified neurologic impairment.

Example 19 includes the methods of any one or any combination of Examples 11-18, further including obtaining imaging data from the infant during feeding while measuring the pressure produced by the infant sucking on the nipple and correlating information based on the pressure signal with information based on the imaging data.

Example 20 includes the methods of any one or any combination of Examples 11-19, further including training a machine learning model for extracting infant feeding data using the correlated information based on the pressure signal with the information based on the imaging data.

Example 21 includes the methods of any one or any combination of Examples 11-20, wherein the training the machine learning model includes using human clinician input received via a user interface for evaluating an infant feeding indication or metric based at least in part on the imaging data.

Example 22 includes the methods of any one or any combination of Examples 11-21, wherein the training the machine learning model includes using human clinician input received via a user interface for evaluating an infant feeding indication or metric based at least in part on the pressure signal.

Example 23 includes the methods of any one or any combination of Examples 11-22 wherein the training the machine learning model includes using human clinician input received via a user interface for evaluating an infant feeding indication or metric based at least in part on the imaging data and the pressure signal.

Example 24 includes the methods of any one or any combination of Examples 11-23 wherein the training the machine learning model includes using a conditional generative adversarial network (CGAN) for training the machine learning model.

Example 24 includes the methods of any one or any combination of Examples 11-23, wherein extracting infant feeding data from the pressure signal includes using a trained machine learning model trained using correlated information based on the pressure signal with the information based on the imaging data.

Example 25 includes the methods of any one or any combination of Examples 11-24, wherein extracting infant feeding data from the pressure signal includes using a trained machine learning model trained using human clinician input received via a user interface for evaluating an infant feeding indication or metric based at least in part on the imaging data.

Example 26 includes the methods of any one or any combination of Examples 11-25, wherein extracting infant feeding data from the pressure signal includes using a trained machine learning model trained using human clinician input received via a user interface for evaluating an infant feeding indication or metric based at least in part on the pressure signal.

Example 27 includes the methods of any one or any combination of Examples 11-26, wherein extracting infant feeding data from the pressure signal includes using a trained machine learning model trained using human clinician input received via a user interface for evaluating an infant feeding indication or metric based at least in part on the imaging data and the pressure signal.

Example 28 includes the methods of any one or any combination of Examples 11-27, wherein extracting infant feeding data from the pressure signal includes using a trained machine learning model trained using a conditional generative adversarial network (CGAN) for training the machine learning model.

Example 29 includes the methods of any one or any combination of Examples 11-28, wherein extracting infant feeding data includes using a trained machine learning model for extracting information about one or any combination of infant sucking and swallowing.

Example 30 includes the methods of any one or any combination of Examples 11-29, further including using a trained machine learning model for correlating the pressure in the passage to one of a nonnutritive suck or a nutritive suck.

Example 31 includes the methods of any one or any combination of Examples 11-30, further including using a trained machine learning model for evaluating or displaying, or both, one or any combination of suction amplitude, feeding duration, sucking frequency, swallowing frequency, sucks per swallow, oral bolus hold, initiation of pharyngeal swallow, pharyngeal contraction, tongue base retraction, pharyngeal stripping wave, soft palate elevation, nasopharyngeal regurgitation, pharyngeal residue, tongue fasciculation, bolus airway entry, or upper esophageal segment opening.

Example 32 includes the methods of any one or any combination of Examples 11-31, further including using a trained machine learning model for evaluating or displaying, or both, an infant feeding metric of a particular infant being monitored relative to a peer group or population group, the infant feeding metric including one or any combination of a proficiency metric, an efficiency metric, a rate of transfer metric, or an overall transfer metric.

Example 33 includes the methods of any one or any combination of Examples 11-32, further including using a trained machine learning model for providing information based on the pressure signal includes predicting and displaying one or any combination of: a time to hospital discharge, an alternative nutrition need metric at discharge, an alternative nutrition need metric at one or more specified post-discharge time intervals, a future developmental delay metric, a risk of future oral nutrition deficit metric, a risk of future cardiopulmonary stability metric, or a risk of hospital readmission for feeding difficulty metric.

Example 34 includes the methods of any one or any combination of Examples 11-33, further including using a trained machine learning model for evaluating or displaying, or both, an indication of an infant feeding phenotype according to a dysphagia-associated disease state including one or any combination of: cleft of hard or soft palate, spinal muscular atrophy, cerebral palsy. Down syndrome, DiGeorge syndrome. Pierre Robin sequence, a specified genetic anomaly, congenital heart defect, or a specified neurologic impairment.

Example 35 includes the methods of any one or any combination of Examples 11-34, further including using a trained machine learning model for identifying or prioritizing one or more recommendations to improve or maximize infant feeding performance, the one or more recommendations including one or any combination of: bottle nipple type, bottle type, feeding position, feeding duration, pacing, volume per feeding session, feeding fluid characteristic, or alternative nutrition.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to an example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An apparatus comprising:
  an infant feeding nipple comprising a flexible nipple wall extending between a feeding end and a bottle end and wherein an internal surface of the nipple wall defines a nipple cavity that is shaped to generally mirror an external surface of the nipple wall, the feeding end defining an opening of a feeding passage, the feeding passage extending through the nipple wall to receive fluid for feeding the infant, the nipple further comprising a pressure-sensing passage, formed by and within the nipple wall, the pressure-sensing passage extending from the feeding end to an opening to an intraoral suction pressure sensor,
  the pressure sensor engageable into the nipple at the bottle end of the nipple in communication with the pressure-sensing passage to transduce an intraoral suction pressure in the pressure-sensing passage into a transduced intraoral suction pressure signal,
  wherein the pressure-sensing passage is integrated and embedded within the nipple wall and is separate from the feeding passage and includes a pressure-sensing opening at the feeding end that is adjacent to and separate from the opening of the feeding passage, such that the intraoral suction pressure produced within a mouth of the infant is transmitted within an open conduit formed via the pressure-sensing opening and via the pressure-sensing passage within the nipple wall to the pressure sensor for measurement by the pressure sensor of the intraoral suction pressure produced within the mouth of the infant.

2. The apparatus of claim 1, further comprising a communication circuitry module electrically connected to the pressure sensor and configured to process the pressure signal to provide infant feeding data.

3. The apparatus of claim 2, further comprising a user interface for receiving information from the communication circuitry module and displaying the infant feeding data to a user.

4. The apparatus of claim 3, wherein the communication circuitry module and the user interface respectively include wireless communication circuitry to communicate therebetween information based on the pressure signal.

5. The apparatus of claim 1, further comprising a collar for attaching the nipple to a bottle at the bottle end of the nipple, wherein the collar fits around the pressure sensor.

6. The apparatus of claim 5, wherein the collar comprises:
  a snap for securing the pressure sensor;
  a first notch for aligning the pressure sensor with the collar; and
  a second notch for aligning the nipple with the collar.

7. The apparatus of claim 1, wherein the pressure sensor includes an elastic membrane.

8. A method for monitoring infant feeding, the method comprising:
  measuring an intraoral suction pressure, produced within a mouth of an infant by the infant sucking on a nipple device, via a pressure-sensing passage formed by and embedded within a nipple wall, wherein the nipple wall includes an internal surface defining a nipple cavity that is shaped to generally mirror an external surface of the nipple wall, the pressure-sensing passage being separate from a feeding passage extending through the nipple wall, wherein the measuring the intraoral suction pressure comprises sensing the intraoral suction pressure produced within the mouth of the infant and transmitted via the pressure-sensing passage to a pressure sensor, the pressure-sensing passage including a pressure-sensing opening that is separate from and adjacent to the feeding passage through the nipple wall at a feeding end of the nipple device, the pressure sensor located in or adjacent the nipple device, the pressure sensor engageable into the nipple device at a bottle end of the nipple device such that the pressure sensor is in communication with the pressure-sensing passage to transduce the intraoral suction pressure in the pressure-sensing passage into a transduced suction pressure signal;

transducing the intraoral suction pressure produced within the mouth of the infant transmitted to and measured by the pressure sensor in communication with the pressure-sensing passage into the transduced suction pressure signal;

extracting infant feeding data from the transduced suction pressure signal; and providing information based on the transduced suction pressure signal for one or any combination of display to a user, further signal processing, storage, or tracking.

9. The method of claim 8, wherein extracting the infant feeding data includes extracting information about one or any combination of infant sucking or swallowing.

10. The method of claim 8, wherein extracting the infant feeding data includes correlating the intraoral suction pressure in the pressure-sensing passage to one of a nonnutritive suck or a nutritive suck.

11. The method of claim 8, wherein extracting the infant feeding data comprises evaluating or displaying, or both, one or any combination of suck amplitude, suck generation, suck release rate, suck duration, suck generation duration, feeding duration, milk ejection pressure, suck integral, suck burst length, burst break length, suck peaks metric, suck spectral arc length, suck frequency, lingual fasciculations, sucks per swallow, suck rhythmicity, swallow frequency, swallow rhythmicity, oral bolus hold, initiation of pharyngeal swallow, tongue base retraction, pharyngeal contraction, tongue base retraction, pharyngeal stripping wave, soft palate elevation, nasopharyngeal regurgitation, pharyngeal residue, bolus airway entry penetration, bolus airway entry aspiration, or upper esophageal segment opening.

12. The method of claim 8, wherein providing the information based on the transduced suction pressure signal includes predicting and displaying one or any combination of:

a time to hospital discharge, an alternative nutrition need metric at discharge, an alternative nutrition need metric at one or more specified post-discharge time intervals, a future developmental delay metric, a risk of future oral nutrition deficit metric, a risk of future cardiopulmonary stability metric, or a risk of hospital readmission for feeding difficulty metric.

13. The method of claim 8, further comprising evaluating or displaying, or both, an infant feeding metric of a particular infant being monitored relative to a peer group or population group, the infant feeding metric including one or any combination of a proficiency metric, an efficiency metric, a rate of transfer metric, or an overall transfer metric.

14. The method of claim 8, further comprising identifying or prioritizing one or more recommendations to improve or maximize infant feeding performance, the one or more recommendations including one or any combination of: bottle nipple type, bottle type, feeding position, feeding duration, pacing, volume per feeding session, feeding fluid characteristic, oral motor exercises, or alternative nutrition.

15. The method of claim 8, further comprising evaluating or displaying, or both, an indication of an infant feeding phenotype according to a dysphagia-associated disease state including one or any combination of: cleft of hard or soft palate, spinal muscular atrophy, cerebral palsy, Down syndrome, DiGeorge syndrome, Pierre Robin sequence, a specified genetic anomaly, congenital heart defect, or a specified neurologic impairment.

16. The method of claim 8, further comprising:

obtaining imaging data from the infant during feeding while measuring the intraoral suction pressure produced by the infant sucking on the nipple device; and correlating information based on the transduced suction pressure signal with information based on the imaging data.

17. The method of claim 16, comprising training a machine learning model for extracting the infant feeding data using the correlated information based on the transduced suction pressure signal with the information based on the imaging data.

18. The method of claim 17, wherein training the machine learning model includes using human clinician input received via a user interface for evaluating an infant feeding indication or metric based at least in part on the imaging data, the transduced suction pressure signal, or both.

19. The method of claim 16, wherein extracting the infant feeding data from the transduced suction pressure signal includes using a trained machine learning model trained using the correlated information based on the transduced suction pressure signal with the information based on the imaging data.

20. The method of claim 18, wherein extracting the infant feeding data from the transduced suction pressure signal includes using a trained machine learning model trained using human clinician input received via a user interface for evaluating an infant feeding indication or metric based at least in part on the imaging data, the transduced suction pressure signal, or both.

21. The method of claim 8, wherein extracting the infant feeding data includes using a trained machine learning model for extracting information about one or any combination of infant sucking and swallowing.

22. The method of claim 8, comprising using a trained machine learning model for correlating the intraoral suction pressure in the pressure-sensing passage to one of a nonnutritive suck or a nutritive suck.

23. The method of claim 8, comprising using a trained machine learning model for evaluating or displaying, or both, one or any combination of suction amplitude, feeding duration, sucking frequency, swallowing frequency, sucks per swallow, oral bolus hold, initiation of pharyngeal swallow, pharyngeal contraction, tongue base retraction, pharyngeal stripping wave, soft palate elevation, nasopharyngeal regurgitation, pharyngeal residue, tongue fasciculation, bolus airway entry, or upper esophageal segment opening.

24. The method of claim 8, comprising using a trained machine learning model for evaluating or displaying, or both, an infant feeding metric of a particular infant being monitored relative to a peer group or population group, the infant feeding metric including one or any combination of a proficiency metric, an efficiency metric, a rate of transfer metric, or an overall transfer metric.

25. The method of claim 8, comprising using a trained machine learning model for providing the information based on the transduced suction pressure signal includes predicting and displaying one or any combination of: a time to hospital discharge, an alternative nutrition need metric at discharge, an alternative nutrition need metric at one or more specified post-discharge time intervals, a future developmental delay metric, a risk of future oral nutrition deficit metric, a risk of future cardiopulmonary stability metric, or a risk of hospital readmission for feeding difficulty metric.

26. The method of claim 8, comprising using a trained machine learning model for evaluating or displaying, or both, an indication of an infant feeding phenotype according to a dysphagia-associated disease state including one or any combination of: cleft of hard or soft palate, spinal muscular atrophy, cerebral palsy, Down syndrome, DiGeorge syndrome, Pierre Robin sequence, a specified genetic anomaly, congenital heart defect, or a specified neurologic impairment.

27. The method of claim 8, comprising using a trained machine learning model for identifying or prioritizing one or more recommendations to improve or maximize infant feeding performance, the one or more recommendations including one or any combination of: bottle nipple type, bottle type, feeding position, feeding duration, pacing, volume per feeding session, feeding fluid characteristic, or alternative nutrition.

\* \* \* \* \*